(12) United States Patent
Chambers et al.

(10) Patent No.: US 6,379,513 B1
(45) Date of Patent: Apr. 30, 2002

(54) SENSOR CONNECTION MEANS

(75) Inventors: Garry Chambers; Alastair McIndoe Hodges, both of San Diego, CA (US); Thomas William Beck, North Richmond; Ian Andrew Maxwell, Five Dock, both of (AU)

(73) Assignee: USF Filtration and Separations Group Inc., Timonium, MD (US)

( * ) Notice: Subject to any disclaimer, the term of this patent is extended or adjusted under 35 U.S.C. 154(b) by 0 days.

(21) Appl. No.: 09/399,512

(22) Filed: Sep. 20, 1999

Related U.S. Application Data

(63) Continuation of application No. PCT/AU98/00184, filed on Mar. 20, 1998.

(30) Foreign Application Priority Data

Mar. 21, 1997 (AU) .............................................. PO5813

(51) Int. Cl.[7] .............................................. G01N 27/26
(52) U.S. Cl. ........................ 204/400; 204/403; 204/416; 324/450
(58) Field of Search ................................ 204/400, 403, 204/416; 324/437, 450

(56) References Cited

U.S. PATENT DOCUMENTS

| | | | |
|---|---|---|---|
| 4,301,412 A | 11/1981 | Hill et al. | |
| 4,301,414 A | 11/1981 | Hill et al. | |

(List continued on next page.)

FOREIGN PATENT DOCUMENTS

| | | |
|---|---|---|
| AU | A-54873/94 | 8/1994 |
| EP | 0 170 375 B1 | 2/1986 |
| EP | 0 351 516 A2 | 1/1990 |
| EP | 0 351 892 A2 | 1/1990 |
| EP | 0 560 336 A1 | 3/1993 |
| WO | WO 89/08713 | 9/1989 |
| WO | WO 95/16198 | 6/1995 |
| WO | WO 95/28634 | 10/1995 |
| WO | WO 97/00441 | 1/1997 |
| WO | WO 97/18464 | 5/1997 |
| WO | WO 97/18465 | 5/1997 |

OTHER PUBLICATIONS

Supplementary European Search Report –(EP 98 90 7775).

*Primary Examiner*—Jill Warden
*Assistant Examiner*—Alex Noguerola
(74) *Attorney, Agent, or Firm*—Knobbe, Martens, Olson, and Bear LLP

(57) ABSTRACT

The invention relates to a sensor adapted for electrical connection to a power source having an electrical contact means (3). The sensor has a first insulating substrate (1) carrying a first electrode (2) and a second insulating substrate (7) carrying a second electrode (6). The electrodes are disposed to face each other in spaced apart relationship, sandwiching a spacer (4) therebetween. A first cut-out portion extends through the first insulating substrate (1) and a spacer (4) to expose a first contact area (23) on the second insulating substrate (7). This permits the electrical contact means (31) to effect electrical connection with the first contact (23) which in turn is in electrically conductive connection with the second electrode (6). A similar contact arrangement may be disposed on the opposite side of the sensor.

23 Claims, 4 Drawing Sheets

U.S. PATENT DOCUMENTS

| | | |
|---|---|---|
| 4,303,887 A | 12/1981 | Hill et al. |
| 4,900,424 A | 2/1990 | Birth et al. |
| 5,120,420 A | 6/1992 | Nankai et al. |
| 5,126,034 A | 6/1992 | Carter et al. |
| 5,128,015 A | 7/1992 | Szuminsky et al. |
| 5,141,868 A | 8/1992 | Shanks et al. |
| 5,192,415 A | 3/1993 | Yoshioka et al. |
| 5,229,282 A | 7/1993 | Yoshioka et al. |
| 5,320,732 A | 6/1994 | Nankai et al. |
| 5,382,346 A | 1/1995 | Uenoyama et al. |
| 5,384,028 A | 1/1995 | Ito |
| 5,385,846 A | 1/1995 | Kuhn et al. |
| 5,413,690 A | 5/1995 | Kost et al. |
| 5,437,999 A | 8/1995 | Diebold et al. |
| 5,502,396 A * | 3/1996 | Desarzens et al. .......... 324/713 |
| 5,508,171 A | 4/1996 | Walling et al. |
| 5,509,410 A | 4/1996 | Hill et al. |
| 5,628,890 A | 5/1997 | Carter et al. |
| 5,645,709 A | 7/1997 | Birch et al. |
| 5,997,817 A | 12/1999 | Crismore et al. |

* cited by examiner

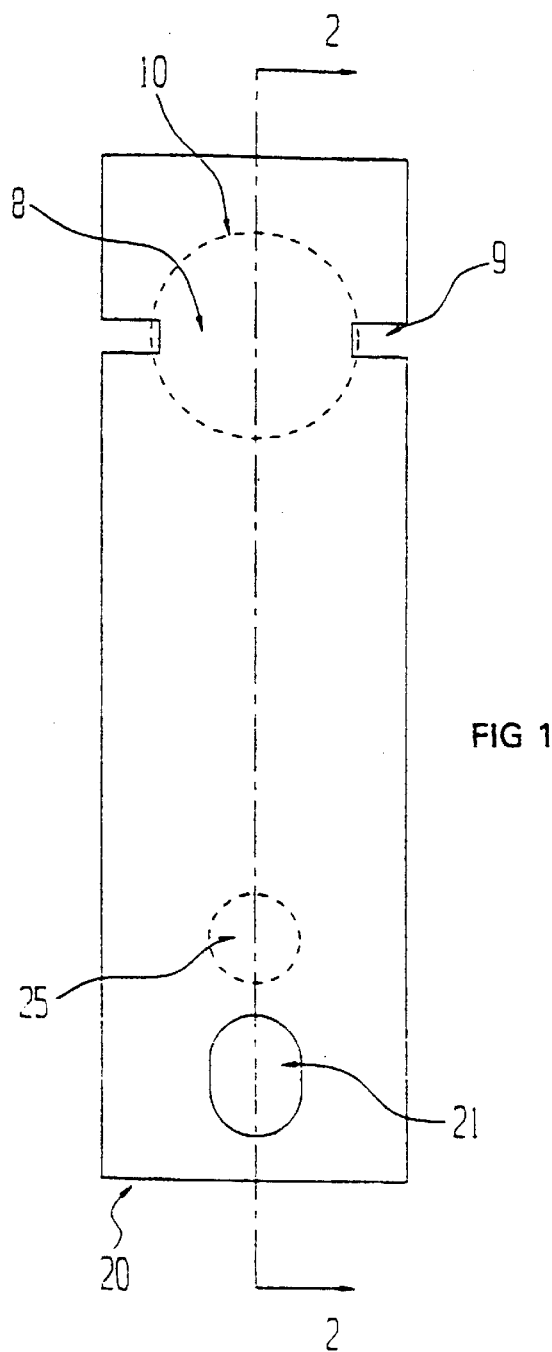
FIG 1
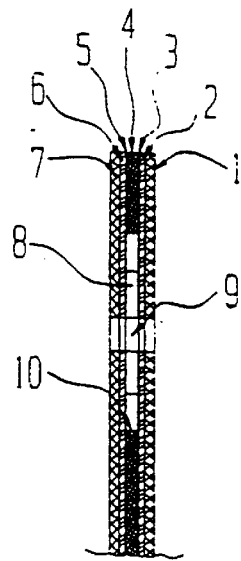
FIG 2
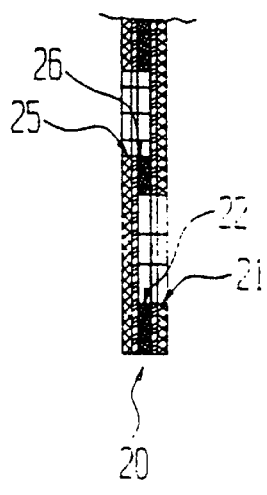

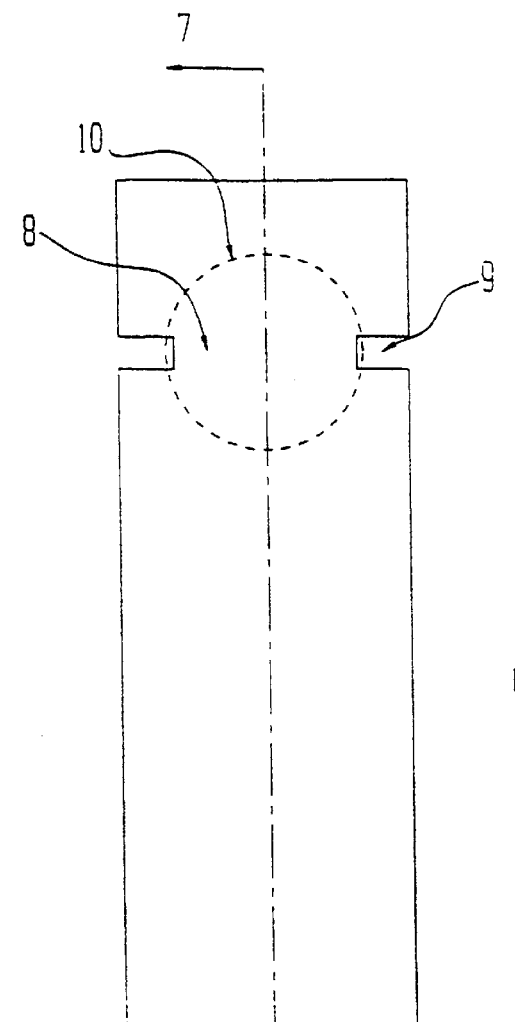
FIG 5
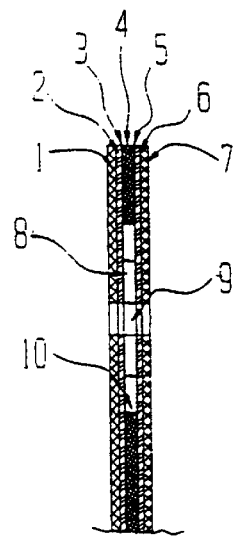
FIG 7
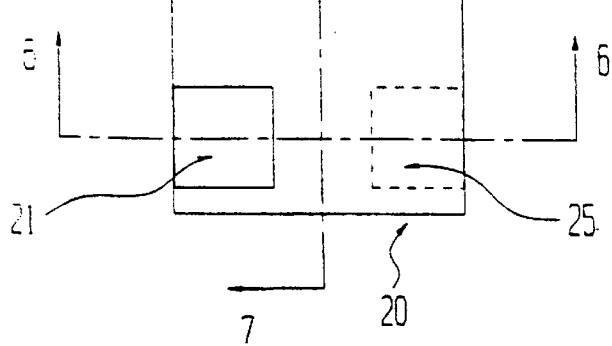

SENSOR CONNECTION MEANS

RELATED APPLICATIONS

This application is a continuation application of International Patent Application No. PCT/AU98/00184, internationally filed Mar. 20, 1998, and claiming priority from Australian Provisional Patent Application No. PO 5813, filed Mar. 21, 1997.

TECHNICAL FIELD

This invention relates to disposable electrochemical sensors of the type used for quantitative analysis, for example, of glucose levels in blood, for pH measurement, or the like. More particularly the invention relates to means for electrical connection of such sensors to a measuring apparatus.

BACKGROUND ART

U.S. Pat. No. 5,437,999 discloses an electrochemical sensor of the kind which in use is electrically connected with a power source. The sensor is constructed from two spaced apart printed circuit boards each having a metal layer on one side and disposed so that the metal layers are facing each other in spaced apart relationship. The metal layers are photolithographically treated to define electrode areas which form part of a cell. At one end of the assembly the electrode substrates are cut to provide laterally spaced protruding tabs bearing the metal layer. The exposed metal surfaces of the tabs act as contact pads, each contact pad being electrically connected with a corresponding electrode. The contact pads in turn engage contact prongs connected to a power source and provide electrical connection between the sensor and a power source.

The arrangement of U.S. Pat. No. 5,437,999 suffers from the disadvantages that the substrate is required to be of considerable rigidity in order to ensure satisfactory and reliable electrical contact. Moreover the user is often left uncertain as to whether a sensor has satisfactorily been connected with the power source.

In co-pending applications PCT/AU96/00207, PCT/AU96/00365, PCT/AU96/00723 and PCT/AU96/00724 there are described various very thin electrochemical cells. Each cell is defined between facing spaced apart electrodes which are formed as thin metal coatings (for example sputter coatings) deposited on thin inert plastic film (for example 100 micron thick PET). The electrodes are separated one from the other by a spacer of thickness of for example 500 µm or less.

The connection arrangement of U.S. Pat. No. 5,437,999 is not suitable for use with the extremely thin sensor devices of the kind discussed in our co-pending applications in view of the flexibility of the insulating electrode carriers. In general, it is desirable that the disposable sensor be capable of simple, quick, reliable and effective connection with the power source in the measuring device by unskilled users. It is an object of the present invention to overcome or ameliorate at least one of the disadvantages of the prior art, or to provide a useful alternative.

DESCRIPTION OF THE INVENTION

According to a first aspect, the invention provides a sensor adapted for electrical connection with a power source having first contact means, the sensor comprising:

a first insulating substrate carrying a first electrode and a second insulating substrate carrying a second electrode, said electrodes being disposed to face each other in spaced apart relationship, a first cut-out portion extending through said first insulating substrate and a spacer to expose a first contact area on the second insulating substrate to permit a first contact means to effect electrical connection with the first contact area disposed on the second insulating substrate, the first contact area being in electrically conductive connection with the second electrode.

The first contact area may be maintained at a predetermined depth from the first insulating substrate.

According to a second aspect, the invention provides a sensor according to the first aspect further comprising a second cut-out portion extending through said second insulating substrate and the, or another, spacer to expose a second contact area on the first insulating substrate to permit a second contact means to effect electrical connection with a second contact area disposed on the first insulating substrate, the second contact area being in electrically conductive connection with the first electrode.

The second contact area may be maintained at a predetermined depth from the second insulating substrate.

According to a third aspect, the invention also provides a sensing system comprising a sensor according to the first or second aspects and a sensing apparatus including a first contact means and/or second contact means adapted to effect electrical contact with the first and second contact areas respectively.

"Comprising" as herein used is used in an inclusive sense, that is to say in the sense of "including" or "containing." The term is not intended in an exclusive sense ("consisting of" or "composed of").

In preferred embodiments the insulating substrate is made of a flexible insulating material. The second electrode and the first contact area are formed from a unified layer of metal deposited on the first substrate, and more preferably deposited by being sputter coated thereon. Suitable metals include, but are not limited to palladium, gold, platinum, iridium, and silver. Carbon may also be used. Desirably the contactor is a metal contactor which is resiliently biased to extend through the first cut-out portion to make contact with the metal first contact area on the second substrate. In highly preferred embodiments the contactor is adapted for click engagement with the cut-out portion which extends through the first insulating substrate and the spacer.

With a connector according to the current invention the spacer layer provides extra strength. A rigid connector can therefore be formed using flexible materials. This allows a wider range of materials to be utilized. An audible confirmation of connection can also be simply provided by the current invention unlike the connector described in U.S. Pat. No. 5,437,999.

BRIEF DESCRIPTION OF THE DRAWINGS

The invention will now be described by way of example only with reference to the accompanying drawings in which:

FIG. 1 shows a first embodiment of a sensor according to the invention in plan view.

FIG. 2 shows a scrap side elevation of the sensor of FIG. 1 in cross-section on line 10—10.

FIG. 5 shows a second embodiment of the invention in plan view.

FIG. 7 shows a cross-section of the embodiment of FIG. 5 in side elevation on line D—D.

BEST MODES FOR CARRYING OUT THE INVENTION

Figure 4:
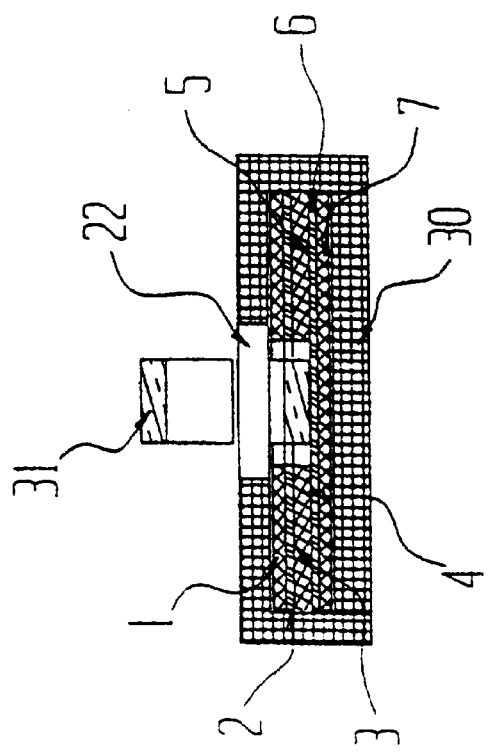
FIG. 4 shows an end elevation of the sensor of FIG. 3 in section on line A—A.
Figure 3:
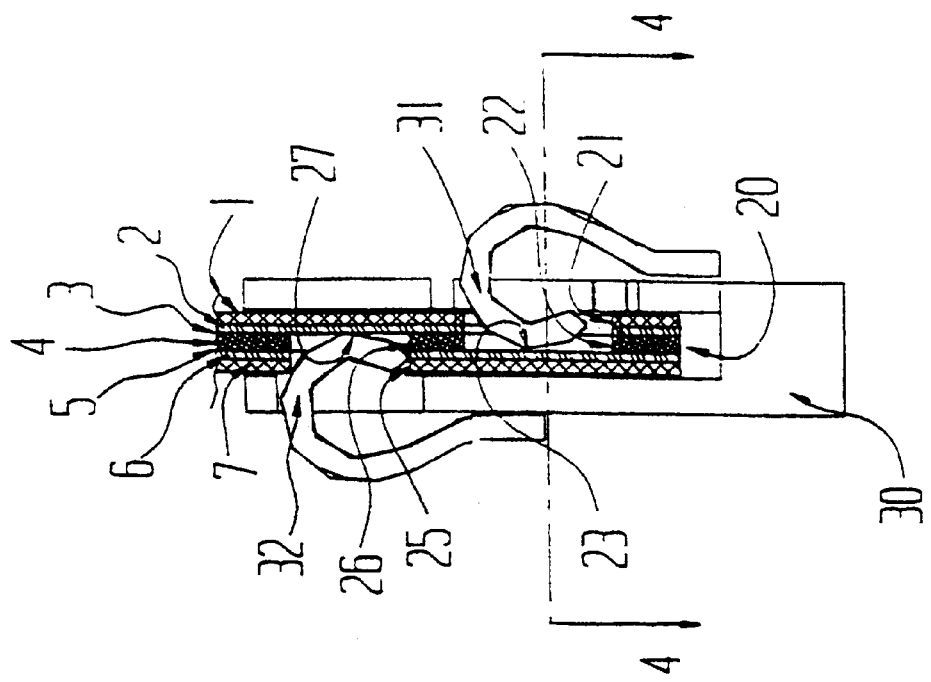
FIG. 3 is a diagrammatic enlargement showing a part of the sensor of FIG. 2 in engagement with contacts.

With reference to FIGS. 1 to 3 there is shown a first embodiment of an electrochemical sensor. The sensor comprises a polyester spacer 4 approximately 25 mm×5 mm and 100 microns thick and having a circular aperture 8 of 3.4 mm diameter. Aperture 8 defines a cylindrical cell wall 10. Adhered to one side of spacer 4 is a first insulating substrate polyester sheet 1 having a first coating of palladium 2. The palladium was sputter coated on sheet 1 at between 4 and 5 millibar pressure in an atmosphere of argon gas to give a uniform coating thickness of about 100–1000 angstroms. Sheet 1 is adhered by means of adhesive 3 to spacer 4 with palladium coating 2 adjacent spacer 4 and covering one side of aperture 8.

A second insulating substrate 7 consists of a polyester sheet having a second sputter coating 6 of palladium adhered by means of contact adhesive 5 to the other side of spacer 4 and covering the opposite side of aperture 8. There is thereby defined a cell having cylindrical side wall 10 and closed at one cylinder end by a first electrode of palladium metal 2. The other cylinder end wall is a second electrode formed from palladium 6. The assembly is notched at 9 to provide a means for admission of a solution to the cell, and to allow air to escape.

Adjacent one end 20 a cut-out aperture 21 pierces first insulating layer 1 and first metal layer 2. In the present example cut-out 21 is oval-shaped. A corresponding cut-out portion 22 in spacer 4 is in registration with cut-out 21. FIG. 3 shows a side elevation cross-section of sensor 1 inserted into a receiving slot formed in part 30 of measuring apparatus and to which is mounted a first resilient contactor 31 and a second resilient contactor 32. Upon insertion of sensor end 20 into the slot, contactor 31 rides over the outer surface of insulating layer 1 and clicks into the well formed by apertures 21 and 22 to engage a first contact area portion 23 of metal layer 6. First contact area 23 is a portion of the same metal layer 6 deposited on insulating layer 7 from which the second electrode is formed and is therefore in electrically conductive communication with the second electrode area of cell 8. Contact area 23 is in effect defined by the diameter of cut-out 20 of spacer 4 in the present example.

In the embodiment shown in FIG. 1 a second circular cut-out portion 25 spaced further from edge 20 than aperture 21 extends through second insulating layer 7 and second metal layer 6. A cut-out portion 26 (see FIG. 2) of spacer 4 corresponds with an registers with cut-out portion 25 of insulating layer 7. Referring again to FIG. 3, in use the sensor is configured to permit a second resiliently biased contactor 32 to extend through the well defined by cut-out portions 25 and 26 whereby resilient contactor 32 engages and makes electrical contact with metal layer 2 at 27 and thereby with the first electrode 2 of cell 8.

Resilient connectors 31 and 32 are arranged in a slot 30 of the measuring device and are electrically connected in a measuring circuit. In use, the sensor is inserted into slot 30 with edge 20 leading. The first resilient contactor 31 rides over the end margin of the sensor 1 until it encounters first aperture 21, 22 whereupon it click engages with the opening and makes electrical contact with the first contact area 23 of metal layer 6. Slight additional insertion of sensor 1 in slot 30 causes the second contactor 32 to click engage with the second aperture 25, 26 and make contact with second contact area 27 of metal layer 2.

Spacer 4 surrounds both apertures and ensures that, despite the intrinsic flexibility of the insulating layers and the thinness of the sensor, electrical contact can be made with reliable precision.

Figure 6:
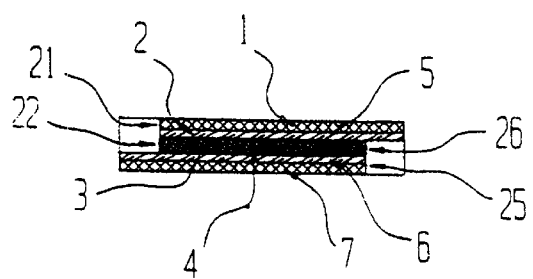
FIG. 6 shows a cross-section of the embodiment of FIG. 5 in end elevation when viewed on line C—C.

A second embodiment of the invention is shown in FIGS. 5, 6 and 7 wherein parts corresponding in function to corresponding parts of the embodiment of FIGS. 1 and 2 are identified by corresponding numerals. The major difference between the second embodiment and the first is that in the second embodiment cut-out portions 21, 22 are cut from one side edge of sensor 1 while cut-out portions 25, 26 are cut out from the opposite side edge of the sensor 1. In this case contactors 31 and 32 are spaced laterally and click substantially simultaneously into their respective cut-out opening. The cut-out openings are surrounded on three sides by spacer 4, the fourth side being exposed at respective edges of the sensor.

Although in the embodiment shown in FIGS. 5, 6 and 7 the openings are at a corresponding distance from end 20 in other embodiments they could be spaced in the longitudinal direction as is the case in the first described embodiment. This ensures that contact is only made when the sensor is inserted in a correct orientation and ensures correct polarity.

Figure 8:
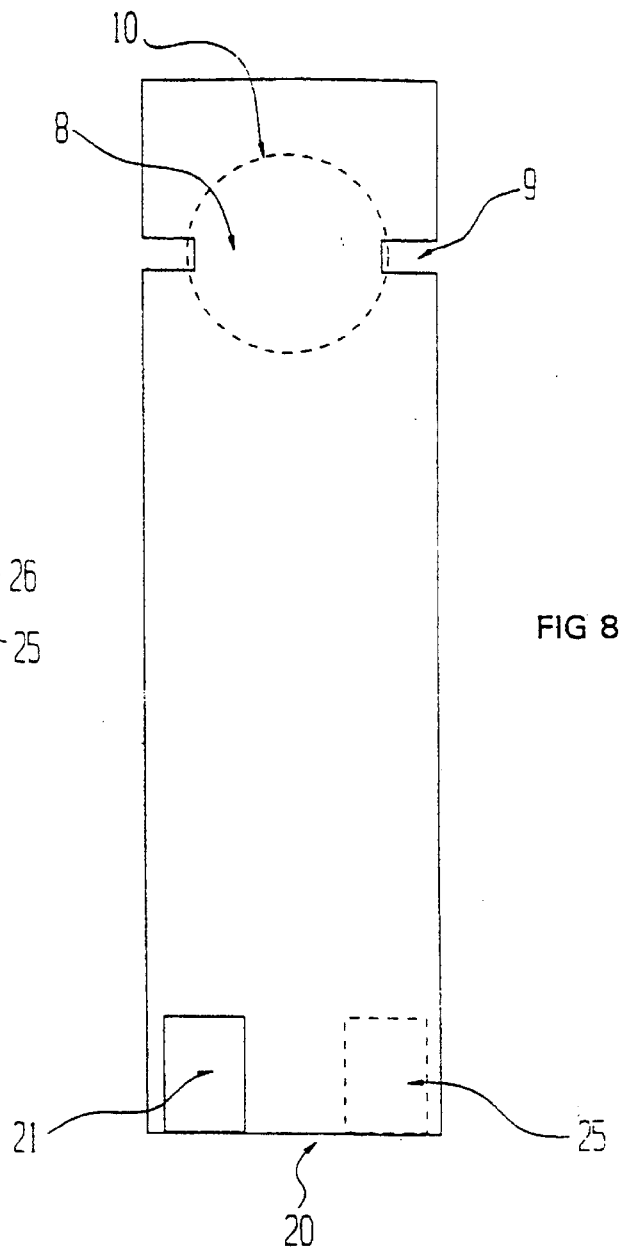
FIG. 8 shows a third embodiment of the invention in plan view.

A third embodiment is shown schematically in FIG. 8. In this case the openings take the form of slots 21, 25 extending longitudinally from edge 20. For preference spacer 4 extends around all edges of openings 21 and 25 of FIG. 8 but in a less preferred embodiment spacer 4 only extends on three sides of slots 21 and 25 in which case click engagement is not obtained or is obtained only if the contacts extend from the opposite direction. However, the advantage that the contact pad area of the sensor is at a predetermined dimension from the opposite face is maintained. If desired the slots can differ in length and co-operation with contacts spaced longitudinally so that contact with both contacts requires correctly orientated insertion of the sensor.

It will be understood that both construction materials and dimensions are given merely by way of example and that sensors of a differing design or construction may utilize the invention. One, two or more than two contacts may be provided by the means shown. The invention extends to include a power source or measuring device when connected to a sensor by the means described. Any suitable form of contactor may be used with sensors according to the invention.

The claims of the invention are as follows:

1. A sensor adapted for electrical connection with a power source having first contact means, the sensor comprising:

a first insulating substrate carrying a first electrode and a second insulating substrate carrying a second electrode, said electrodes being disposed to face each other in spaced apart relationship, a first cut-out portion extending through said first insulating substrate and a spacer to expose a first contact area on the second insulating substrate to permit a first contact means to effect electrical connection with the first contact area disposed on the second insulating substrate, the first contact area being in electrically conductive connection with the second electrode; and a second cut-out portion extending through said second insulating substrate and the, or another, spacer to expose a second contact area on the first insulating substrate to permit a second contact means to effect electrical connection with the second contact area disposed on the first insulating substrate, the second contact area being in electrically conductive connection with the first electrode.

2. A sensor according to claim 1 wherein the first cut-out portion is elongated relative to the second cut-out portion such that during sliding engagement of the sensor with said first and second contact means a first click engagement occurs between the first contact means and first contact area, followed by the first contact means sliding over the first contact area until a second click engagement occurs between the second contact means and second contact area.

3. A sensor according to claim 1 wherein the first contact area is maintained at a predetermined depth from the first insulating substrate.

4. A sensor according to claim 1 wherein the second contact area is maintained at a predetermined depth from the second insulating substrate.

5. A sensor according to claim 1 wherein each insulating substrate is made of a flexible insulating material.

6. A sensor according to claim 5 wherein the flexible insulating material is polyester.

7. A sensor according to claim 1 wherein each electrode and its respective contact area are formed from a layer of metal deposited on the insulating substrate.

8. A sensor according to claim 7 wherein the metal is selected from the group consisting of palladium, gold, platinum, iridium and silver.

9. A sensor according to claim 7 wherein the metal is 10–1000 nanometers thick.

10. A sensor according to claim 7 wherein the layer of metal is deposited on the substrate by sputter coating.

11. A sensor according to claim 1 wherein each electrode and its respective contact area are formed from carbon.

12. A sensor according to claim 1 wherein the cut-out portions are laterally spaced apart relative to the longitudinal axis of the sensor.

13. A sensor according to claim 1 wherein the cut-out portions are longitudinally spaced relative to the longitudinal axis of the sensor.

14. A sensor according to claim 1 wherein the cut-out portions are laterally and longitudinally spaced relative to the longitudinal axis of the sensor.

15. A sensor according to claim 1 wherein at least one of the substrate or spacer extends around the entire periphery of the cut-out portion.

16. A sensor according to claim 1 wherein the cut-out portion is adapted for click engagement with the respective contact means.

17. A sensor according to claim 1 wherein the cut-out portion is cut from an edge of the sensor such that the cut-out portion is open on at least one edge of the sensor.

18. A sensing system comprising a sensor according to claim 1, and a sensing apparatus including a first contact means and/or a second contact means adapted to effect electrical contact with the first and second contact areas respectively.

19. A sensing system according to claim 18 wherein the contact means are resiliently biased to extend through the respective cut-out portion to make contact with the contact area.

20. A sensing system according to claim 18 wherein the contact means are adapted for click engagement with the respective cut-out portions.

21. A sensor adapted for electrical connection with a power source having first contact means, the sensor comprising:

a first insulating substrate carrying a first electrode and a second insulating substrate carrying a second electrode, said electrodes being disposed to face each other in spaced apart relationship, and a first cut-out portion extending through said first insulating substrate and a spacer to expose a first contact area on the second insulating substrate to permit a first contact means to effect electrical connection with the first contact area disposed on the second insulating substrate, the first contact area being in electrically conductive connection with the second electrode, wherein at least one of the substrate or spacer extends around the entire periphery of the cut-out portion.

22. A sensor adapted for electrical connection with a power source having first contact means, the sensor comprising:

a first insulating substrate carrying a first electrode and a second insulating substrate carrying a second electrode, said electrodes being disposed to face each other in spaced apart relationship, and a first cut-out portion extending through said first insulating substrate and a spacer to expose a first contact area on the second insulating substrate to permit a first contact means to effect electrical connection with the first contact area disposed on the second insulating substrate, the first contact area being in electrically conductive connection with the second electrode, wherein the cut-out portion is adapted for click engagement with the contact means.

23. A sensor adapted for electrical connection with a power source having first contact means, the sensor comprising:

a first insulating substrate carrying a first electrode and a second insulating substrate carrying a second electrode, said electrodes being disposed to face each other in spaced apart relationship, and a first cut-out portion extending through said first insulating substrate and a spacer to expose a first contact area on the second insulating substrate to permit a first contact means to effect electrical connection with the first contact area disposed on the second insulating substrate, the first contact area being in electrically conductive connection with the second electrode, wherein the cut-out portion is cut from an edge of the sensor such that the cut-out portion is open on at least one edge of the sensor.

* * * * *